(12) United States Patent
Eugley

(10) Patent No.: US 6,379,305 B1
(45) Date of Patent: Apr. 30, 2002

(54) EARLY-FETAL-HEARTBEAT-DETECTION DEVICE AND METHOD

(76) Inventor: Janet Stoner Eugley, HC 61, Box 1181 Rte. 131, St. George, ME (US) 04857

( * ) Notice: Subject to any disclaimer, the term of this patent is extended or adjusted under 35 U.S.C. 154(b) by 0 days.

(21) Appl. No.: 09/544,256

(22) Filed: Apr. 5, 2000

(51) Int. Cl.⁷ .................................................. A61B 8/02
(52) U.S. Cl. ..................................................... 600/453
(58) Field of Search ......................... 600/437, 453–456, 600/459

(56) References Cited

U.S. PATENT DOCUMENTS

| | | | |
|---|---|---|---|
| 4,413,629 A | | 11/1983 | Durley, III |
| 4,757,823 A | * | 7/1988 | Hofmeister et al. ........ 600/454 |
| 5,630,418 A | | 5/1997 | Lee et al. |
| 5,699,805 A | * | 12/1997 | Seward et al. ............... 600/459 |
| 5,827,969 A | | 10/1998 | Lee et al. |
| 6,210,329 B1 | * | 4/2001 | Christmas et al. .......... 600/437 |

* cited by examiner

*Primary Examiner*—Francis J Jaworski
(74) *Attorney, Agent, or Firm*—Thomas L Bohan; Patricia M Mathers

(57) ABSTRACT

A Doppler fetal heartbeat measurement device and method of use for reliable, convenient and inexpensive detection of fetal heartbeat and measurement of its rate from seven to twelve weeks gestation. The device is a conventional, inexpensive Doppler base unit having an intravaginal probe. Use of the present invention eliminates the need for the expensive procedure of transvaginal ultrasonic imaging for early detection of fetal heartbeat in the event of complications (e.g. cramping, spotting, pain) or the observation of a uterine size that does not correlate to the date of the last menstrual period.

14 Claims, 1 Drawing Sheet

EARLY-FETAL-HEARTBEAT-DETECTION DEVICE AND METHOD

BACKGROUND OF THE INVENTION

1. Field of the Invention

The present invention relates to a portable Doppler fetal heartbeat measurement device and a method of use for early detection of fetal heartbeat. More specifically, this invention relates to the adaptation of an intravaginal probe for use with a standard Doppler fetal heartbeat measurement device base unit and a method of use for detection of fetal heartbeat from seven to twelve weeks gestation.

2. Description of the Related Art

Christian Doppler first described what is now known as the Doppler effect in the 19th century. In the 20th century Doppler's principle has been harnessed in the optical, radio and ultrasound sciences to produce many useful devices. Doppler ultrasound techniques for medical diagnostic purposes are well known. For example, see Atkinson and Woodcock, DOPPLER ULTRASOUND AND ITS USE IN CLINICAL MEASUREMENT, Academic Press, New York City (1982). Also, Durley III (U.S. Pat. No. 4,413,629; issued 1983) disclosed a portable, ultrasonic Doppler device for detecting fetal heartbeat and measuring its rate. The hand-held Doppler fetal heartbeat measurement device (hereafter referred to as a conventional doppler) has since become standard equipment at nearly every obstetrics practice in the United States, because it is a useful, simple and relatively inexpensive device. The conventional doppler consists of essentially two components:(i) a hand-held probe containing one or more transducers or transducer arrays for generating and detecting ultrasonic waves; and (ii) an electronic base unit (hereafter referred to as a base unit) capable of converting the electrical signal from the probe to an audible response meaningful to the human ear. In use, the hand-held probe is held against the abdomen of a woman suspected of being pregnant, with the transducer end of the probe facing in the direction of the suspected fetus. The probe is then activated, resulting in an ultrasonic wave stream (with a typical frequency of 3 MHZ) being directed through the abdominal wall. A portion of this wave stream is reflected back to the probe. If a live fetus is present, the movement of its heart (and of blood through the heart chambers) results in a frequency shift ("Doppler shift") in the waves reflected from that region. The magnitude and sign of the Doppler shift varies with the instantaneous velocity of the sound-wave-reflecting surface and hence, if this surface is that of the fetal heart, the motion of the heart chambers. An audible signal is generated by the base unit from the varying Doppler shift. The base unit may also display a visual readout, e.g. a digital display, of fetal heart rate.

In a typical pregnancy, the conventional doppler is incapable of reliably detecting the fetal heartbeat until about 12 weeks gestation. This is owing primarily to the low level of ultrasonic energy reflected from the first trimester fetal heart and to the high degree of dampening of that energy (ultrasonic impedance) by the abdominal wall of the mother. In the event of complications, or the observation of a uterus size that does not correlate to the date of the last menstrual period, a physician's only option to determine fetal viability is to order a sonogram with an intravaginal probe. This technique allows early visualization and measurement of fetal cardiac activity. It has significant disadvantages, however, in that it is expensive and often requires the patient to be sent to another facility which is inconvenient and delays verification of fetal viability.

The primary approach to solving this problem has been directed at increasing the signal to noise ratio of the conventional doppler. Lee et al. (U.S. Pat. No. 5,630,418; issued 1997) ["Lee I"] discloses a controller for muting break noise in a conventional doppler. Break noise is generated when the probe is moved across the skin surface causing the probe/skin interface to be momentarily broken. Eliminating break noise increases the signal to noise ratio and makes it easier to identify the fetal heartbeat while the physician is seeking the fetal heart (which involves moving the probe across the abdomen). Lee et al. (U.S. Pat. No. 5,827,969; issued 1998) ["Lee II"] teaches a device that uses an abdominal probe with selective power settings, enabling the user to increase the power of the transmitted ultrasonic energy, which increases the reflected signal from the fetal heart. Another approach has been aimed at improving the signal processing techniques used to distinguish the low level fetal heartbeat component from the background noise. While these approaches have improved the sensitivity of the conventional doppler they are inherently limited by the impedance of the mother's abdominal wall and the distance between the probe and fetus, especially in obese patients.

The fetal heart begins beating at approximately six to seven weeks gestation. Medically, it is desirable to detect and measure fetal heartbeat in the patient's first office visit (typically approximately eight weeks gestation). It is particularly desirable in cases of spotting, cramping, pain or other complications to determine whether fetal heartbeat is present and its nature, as a demonstration of fetal viability and as a means of reducing subsequent risk of miscarriage. Further, it offers early peace of mind for the patient, especially those with a history of miscarriage. Further still, it may lead to earlier detection of ectopic and other abnormal pregnancies, possibly allowing non-invasive treatment options and better preservation of patient fertility. As indicated above, however, present technology, though available in the form of full sonography systems, is expensive and inconvenient. The capital investment in sonography equipment is 100 to 200 times the cost of the conventional doppler that is present in every ob-gyn office, even those in rural areas of the country far from medical centers. As a consequence, the charges to the patient are comparably much more expensive. Furthermore, patients in rural areas usually have to travel to another town or city to have this procedure carried out in those instances where the early detection of fetal heartbeat is imperative. One consequence is that on many occasions where it is deemed to be helpful (and in retrospect would have been very useful) it is simply not done.

Therefore, what is needed is an inexpensive, portable device that is capable of reliably detecting fetal heartbeat and measuring its rate as early as seven weeks gestation.

SUMMARY OF THE INVENTION

It is an object of the present invention to provide an inexpensive and convenient method and device for detecting fetal heartbeat and measuring its rate in the first trimester of pregnancy. More particularly, it is the object of the present invention to provide such a method and device capable of detecting and quantifying fetal heartbeat as early as eight weeks gestation for the majority of pregnancies.

The present invention meets its objectives by adapting the conventional doppler. The present inventor has found, through experimentation, that with some modifications to the conventional probe, this new device is highly capable of detecting fetal heartbeat and measuring its rate at seven to eight weeks gestation. Consequently, one embodiment of the method of the present invention is to adapt the probe of the conventional doppler so that it can be used intravaginally. Although there are a number of probe designs for the conventional doppler, all terminate in a blunt, flat region intended to be placed against the outside of the abdomen, and then moved along the outside abdominal wall. Nevertheless, it is possible in many instances, after taking standard steps to ensure an antiseptic surface, to introduce the end of one of the conventional-doppler probes into the vagina and thereby, in many cases, obtain an early detection of the presence and rate of the fetal heartbeat. This is a procedure that has not been previously disclosed or taught.

Although it is possible to use the conventional doppler in the abovedescribed fashion, it tends to be awkward and not applicable to every woman. The device of the present invention is designed to overcome these problems, by adapting the conventional doppler to incorporate a true intravaginal probe. The intravaginal probe of the present invention contains the following elements: (I) a rigid or semi-rigid, elongated body portion, (ii) one or more transducers or transducer arrays for emitting and detecting ultrasonic energy and (iii) a means for transmitting intravaginal probe signal information to the base unit.

By using the conventional doppler base in connection with a modified probe, the device of the present invention achieves its goal of enabling every obstetrician's office to afford a means of early fetal-heart detection. The device of the present invention will cost an amount comparable to the traditional doppler device for detecting fetal heartbeat externally through the abdominal wall: about $600 in the present market. There are a number of enhancements that can enhance the device and method of the present invention. Though these embodiments will increase the cost somewhat of the device, the total price will still be about two orders of magnitude below that of the sonography equipment to which physicians and patients must now turn to for early detection of fetal activity. The enhancements include such things as providing wireless communication between the transducer-containing probe and the electronic base unit. This would give the ultimate in hand-held convenience for the person manipulating the probe. The wireless communication would be carried out by any one of the many known methods presently in use in computer technology and elsewhere, such as radio-based, infrared-light-based and the myriad of other telemetry methods.

The method of the present invention for detecting and quantifying fetal heartbeat as early as seven to eight weeks gestation has the following steps: (i) gently insert the intravaginal probe into the vagina, (ii) activate the electronic base unit so as to produce ultrasonic waves from the probe, (iii) by manipulating the probe, direct an ultrasonic wave stream towards the suspected fetus, (iv) detect the ultrasonic waves reflected from the fetal heart at the intravaginal probe and (v) convert the signal from the intravaginal probe to an audible and/or visual display of fetal heart rate at the base unit. One advantage of the present inventive method is that the ultrasonic impedance between the intravaginal probe and the fetus during examination is low, owing to their close proximity. Therefore, the reflected signal from the fetal heart is more easily separated from background noise. This enables the fetal heartbeat to be reliably detected and its rate quantified several weeks earlier than can be achieved with the conventional abdominal method.

The present invention has been found to be useful in detecting and quantifying the fetal heartbeat in early pregnancy. This means, for example, that if complications arise early in pregnancy, e.g. 8 weeks gestation, the present invention may be used to confirm the presence of fetal heartbeat in any obstetrician's office, without resorting to transvaginal sonography. This has the significant advantages of reducing patient expense, quickly confirming fetal viability (providing immediate peace of mind for the patient) and reducing patient inconvenience.

DETAILED DESCRIPTION OF THE PREFERRED EMBODIMENT

Figure 1:
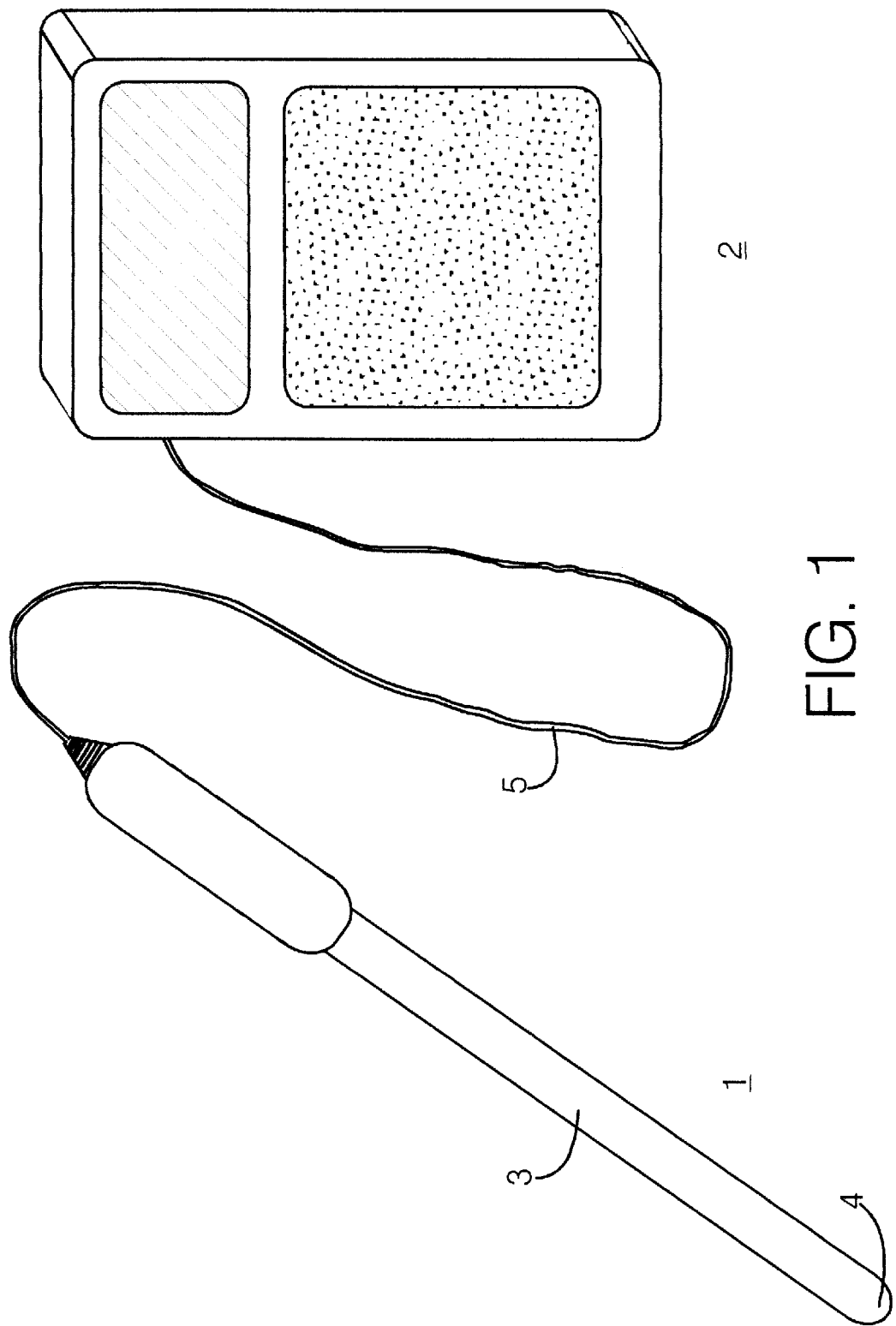
FIG. 1 is an illustration of the device corresponding to the Preferred Embodiment of the present invention.

The Preferred Embodiment of the device of the present invention is shown in FIG. 1. The device includes an intravaginal probe 1 and a conventional base unit 2. Located at the distal end of the probe 1 and internal to the probe 1 is a piezoelectric transducer capable of converting an electrical signal into an ultrasonic signal of a well-defined frequency, constituting the emitted signal. This transducer and its associated circuitry, when activated, detects an incoming ultrasonic signal, the reflected signal, to compare its frequency with that of the emitted signal—the Doppler shift— generates an electronic signal varying with the Doppler shift. Through the cable coupling the probe 1 to the base unit 2, this electronic signal causes the base unit 2 to emit an audible response conveying to the ear of the operator information about the fetal heartbeat.

The device of the Preferred Embodiment of the present invention includes an intravaginal probe 1 that is hand-held and portable and contains the following elements: (I) A rigid or semi-rigid elongated body portion 3, (ii) a transducer 4 for converting electrical signals into ultrasonic energy, and then emitting and detecting ultrasonic energy, and (iii) a means for communicating signal information pertaining to the fetal heartbeat to the base unit. The intravaginal probe 1 of the Preferred Embodiment of the present invention is longer and more slender than the conventional abdominal probe so As to minimize patient discomfort., and to enable greater range to the physician or other caregiver who is manipulating the probe in search of fetal heart action. In particular, in the Preferred Embodiment the elongated body portion 3 has a diameter less than 2.0 cm and a length greater than 12.5 cm. The transducer 4 can be made in accord with any of the transducers and transducer arrays known in the art and presently used in conventional abdominal Doppler fetal heartbeat measurement systems and Doppler imaging systems. In the Preferred Embodiment, they will reside in a transducer housing at the end of the probe 1. The transducer housing is shaped so as to provide good contact with the apex of the vagina when directed towards the uterus. The means for communicating with the base unit in the Preferred Embodiment is a cord 5 containing electrical wires running between the intravaginal probe 1 and the base unit 2. (In other embodiments of the invention, the intravaginal probe 1 is cordless, providing greater flexibility and freedom to the obstetrician, with the means for communicating with the base unit 2 being an infrared, radio or other telemetric signal.) In the Preferred Embodiment, the intravaginal probe 1 contains a handle 6 to allow for easy rotation of the intravaginal probe 1 in the vagina.

In the Preferred Embodiment, a standard conventional doppler fetal heartbeat base is used for the base unit 2. This conventional unit is capable of converting the signal from the intravaginal probe to an audible response meaningful to the human ear.

The present invention further relates to a method for early detecting and quantifying of fetal heartbeat. In the Preferred Embodiment of the present invention, this method consists of the following steps: (I) gently inserting an intravaginal probe 1 into the patient's vagina, (ii) directing an ultrasonic wave stream towards the fetus, (iii) detecting ultrasonic waves reflected from the fetal heart at the intravaginal probe 1 and (iv) converting the signal from the intravaginal probe to an audible signal at the base unit 2.

The details that have been provided here regarding the Preferred Embodiment of the present invention are in no way intended to limit the claimed invention. Anyone skilled in the art can foresee from a reading of the SUMMARY and other portions of this document many equivalent ways of implementing and practicing the present invention.

I claim:

1. An ultrasonic Doppler-shift-based fetal heartbeat detection and measurement device, said device comprising:

a probe having an external shape adapted to facilitate vaginal insertion thereof, and wherein activatable contents of said probe are essentially limited to an activatable Doppler circuit;

a base unit; and a means for conveying signals between said activatable Doppler circuit and said base unit;

wherein said activatable Doppler circuit consists essentially only of those components necessary to generate outgoing ultrasound of an emitted frequency, to detect incoming ultrasound of a reflected frequency, to continuously determine a frequency difference between said emitted frequency and said reflected frequency, to generate a data signal varying in time with said frequency difference, and to deliver said data signal to said means for conveying signals, said means for conveying signals when activated causing said data signal to be delivered to said base unit.

2. The device described in claim 1 wherein said base unit presents a visual display of said data signal as said base unit receives said data signal.

3. The device described in claim 1 wherein said base unit generates an audible sound correlated with said data as said base unit receives said data signal.

4. The device described in claim 3 wherein said means for conveying signals is an electric cable connectable between said base unit and said probe.

5. The device described in claim 3 wherein said means for conveying signals is wireless.

6. The device described in claim 5 wherein said means for conveying signals is radio-based.

7. The device described in claim 5 wherein said means for conveying signals is infrared-based.

8. A method for inexpensive early detection and measurement of fetal heartbeat in a patient thought to be pregnant, said method comprising the steps of:

a) selecting a doppler probe containing an activatable doppler circuit, where said doppler probe is selected from a set consisting of i) a conventional doppler probe from a conventional doppler system and ii) a modified conventional doppler probe differing from said conventional doppler probe in that said modified conventional doppler probe has an outer surface shaped to facilitate intravaginal use thereof;

b) connecting said doppler probe to a base unit of a conventional doppler system by means of a signal-transmitting cable substantially identical to cables used with conventional doppler systems;

c) vaginally inserting said doppler probe into said patient, d) activating said doppler circuit using said base unit, e) positioning said doppler probe so that said doppler circuit is brought into maximum proximity of a suspected fetus, f) listening to and interpreting signals emanating from said base unit, so as to derive information regarding presence and nature of a fetal heartbeat.

9. The method of claim 8 wherein said doppler probe is a conventional doppler probe from a conventional doppler system.

10. The method of claim 8 wherein said doppler probe is a modified conventional doppler probe differing from said conventional doppler probe in that said modified conventional doppler probe has an outer surface shaped to facilitate intravaginal use thereof.

11. An improvement to a conventional doppler system used for external measurements of fetal heartbeat, said conventional doppler system including the combination of a base unit, a flat probe shaped for external abdominal placement and use, and a signals-conveying cable connectable between said base unit and said flat probe, wherein said flat probe contains a probe circuit designed only to generate ultrasonic waves of an emitted frequency, to detect reflected ultrasonic waves of a reflected frequency, and to generate a Doppler signal corresponding to a Doppler shift between said emitted frequency and said reflected frequency, wherein said Doppler signal is conductible from said probe to said base unit via said cable, and wherein said base unit, upon receiving said Doppler signal, produces a notifying signal correlated to said Doppler signal, wherein said notifying signal is interpretable by an operator of said conventional doppler system as giving information about fetal heartbeat, the improvement to said conventional doppler system comprising:

an additional probe to be used in combination with said base unit and said cable of said conventional doppler system, said additional probe differing from said flat probe only in its elongated shape designed to facilitate intravaginal use of said additional probe.

12. The improvement described in claim 11 supplemented by the further improvement comprising;

replacement of said cable with a wireless means of conveying signals between said base unit and said probe, with circuitry necessary to implement said wireless means added to said probe and said base unit, respectively.

13. The improvement described in claim 12 wherein said wireless means is radio-based.

14. The improvement described in claim 12 wherein said wireless means is light-based.

* * * * *